United States Patent
Bright et al.

(12)

(10) Patent No.: US 6,479,688 B2
(45) Date of Patent: Nov. 12, 2002

(54) PROCESS FOR MAKING DI (HYDROXYALKYLARYL) ARYL PHOSPHATE COMPOUNDS

(75) Inventors: Danielle A. Bright, New City, NY (US); Jeffrey E. Telschow, Tarrytown, NY (US)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 10/122,751

(22) Filed: Apr. 15, 2002

(65) Prior Publication Data

US 2002/0151739 A1 Oct. 17, 2002

Related U.S. Application Data

(62) Division of application No. 08/859,856, filed on May 21, 1997, now Pat. No. 6,403,819.

(51) Int. Cl.[7] .................................................. C07F 9/02
(52) U.S. Cl. ........................................................ 558/211
(58) Field of Search .......................................... 558/211

(56) References Cited

FOREIGN PATENT DOCUMENTS

JP           48003905      *  2/1973

* cited by examiner

*Primary Examiner*—T. A. Solola
*Assistant Examiner*—Joseph Murray
(74) *Attorney, Agent, or Firm*—Richard P. Fennelly

(57) ABSTRACT

A process for the formation of a di(hydroxyalkylaryl) aryl phosphate is disclosed which comprises the reaction of an o-alkyl substituted aromatic diol, e.g., an o-alkyl substituted hydroquinone such as o-t-butylhydro-quinone, and monoaryl dihalophosphate, such as monophenyl dichlorophosphate. This process can, in particular, be used to make certain di(hydroxy-o-alkylphenyl) phenyl phosphate compounds, preferably those that are p-hydroxy, such as di(p-hydroxy-o-t-butylphenyl) phenyl phosphate.

4 Claims, No Drawings

PROCESS FOR MAKING DI (HYDROXYALKYLARYL) ARYL PHOSPHATE COMPOUNDS

This is application is a divisional patent application of U.S. Ser. No. 08/859,856, filed on May 21, 1997, and now U.S. Pat. No. 6,403,819.

SUMMARY OF THE INVENTION

The present invention relates to a process for the formation of a di(hydroxyalkylaryl) aryl phosphate which comprises the reaction of an o-alkyl substituted aromatic diol, e.g., an o-alkyl substituted hydroquinone such as o-t-butylhydroquinone, and monoaryl dihalophosphate, such as monophenyl dichlorophosphate. The di(hydroxyalkylaryl) aryl phosphate compositions of this invention are useful as flame retardant additives for thermoplastic and thermoset resins.

The present invention also relates to certain di(hydroxy-o-alkylaryl) aryl phosphate compounds, preferably those that are p-hydroxy, such as di(p-hydroxy-o-t-butylphenyl) phenyl phosphate.

DESCRIPTION OF PREFERRED EMBODIMENTS

As previously described, the invention relates to a process for the formation of a di(hydroxyalkylaryl) arylphosphate which comprises the reaction of an o-alkyl substituted aromatic diol and a monoaryl dihalophosphate.

The o-alkyl substituted aromatic diol contains an alkyl substituent which can be either straight or branched chain of from one to about six carbon atoms in size. Branched structures of from three to six carbon atoms are preferred as exemplified by t-butyl. The hydroxy groups are preferably para- to one another as in hydroquinone. An especially preferred reagent for use is o-t-butylhydroquinone.

The monoaryl dihalophosphate is of the formula ArOP(O)X$_2$, where Ar stands for substituted or unsubstituted aryl, and X stands for halo, such as chloro or bromo. The preferred aryl group is phenyl. A particularly preferred reagent to use is monophenyl dichlorophosphate.

The reaction for forming the desired compounds, which will be described in greater detail below, is between one mole of monoaryl dihalophosphate and two moles of the o-alkyl substituted aromatic diol. This reaction is preferably conducted at an elevated temperature of about 50° C. to about 200° C. using an effective amount (about 0.1% to about 0.5%, by weight of the diarylhalophosphate) of a Lewis acid catalyst, such as magnesium dichloride.

The reaction of the present invention also forms certain di(hydroxy-o-alkylphenyl) phenyl phosphate compounds which are believed to be novel. These compounds can be illustrated, in a preferred embodiment, by the following general formula:

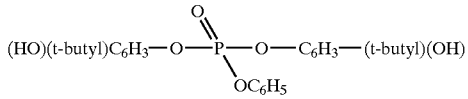

wherein, in a most preferred embodiment, both hydroxy substituents are in the para position and both t-butyl substituents, as the chosen alkyl substituents, are in the ortho position.

The resulting di(hydroxyalkylaryl) arylphosphate product can be used as a reactive type flame retardant for polymer matrices, such as epoxy and polyurethane, and as an additive or reactive-type flame retardant in thermoplastic resins, for example, in polycarbonate resin compositions, including those of the type described in U.S. Ser. No. 08/510,685, filed Aug. 3, 1995. It can be incorporated, for example, in the resin backbone.

The present invention is further illustrated by the Examples which follow.

EXAMPLE 1

Phenyldichlorophosphate (50.0 g, 0.237 mole), t-butylhydroquinone (78.8 g, 0.474 mole), magnesium dichloride (0.3 g) and 200 ml of toluene were added to a 500 ml four-necked flask equipped with a mechanical stirrer, thermometer, reflux condenser, and nitrogen inlet and outlet. The mixture was brought to reflux (about 110° C.), and reflux was maintained for eight hours.

After that period of time had elapsed, a sample from the reactor was analyzed by liquid chromatography. Excluding the solvent, the main product (about 80%) was the desired di(t-butylhydroquinyl)phenyl phosphate. Other impurities included 4.1% by weight of unreacted t-butylhydroquinone and the same amount of di(t-butyl hydroquinone).

Upon evaporation of toluene and addition of methanol, a white solid which melted at 159° C. to 164° C. was isolated. Analysis of the product by $^{13}$C and $^{31}$P NMR gave the following composition: 92.5 wt % of di(t-butylhydroquinyl) phenyl phosphate; 4.8 wt % of t-butylhydroquinyl diphenyl phosphate and 2.7 wt % of triphenyl phosphate.

EXAMPLE 2

The product from Example 1 was evaluated for its effectiveness as a flame retardant in epoxy resin (EPON 828 brand) by the Limiting Oxygen Index (LOI) method. The ratio of epoxy resin to flame retardant was adjusted to produce a 2 wt % phosphorus level in the composite. The epoxy/flame retardant composite was cured using 2-ethyl-4-methyl imidazole as the curing agent. The following results were obtained:

| Epoxy/FR Ratio (Wt. Basis) | % P | LOI |
| --- | --- | --- |
| 100/0 (Control) | 0.0 | 18.5 |
| 70/30 | 2.0 | 26.5 |

EXAMPLE 3

The product from Example 1 was evaluated for its effectiveness as a flame retardant in a high impact polystyrene (HIPS) blend containing polyphenylene ether (PPE) by the LOI method. Blend specimens were prepared by solution casting from chloroform. The following results were obtained:

| HIPS/PPE/FR Ratio (Wt. Basis) | % P | LOI |
| --- | --- | --- |
| 100/0/0 (Control) | 0.0 | 17 |
| 80/20/0 (Control) | 0.0 | 19 |
| 80/20/20 | 1.1 | 22.5 |

EXAMPLE 4

The product from Example 1 was evaluated for its effectiveness as a flame retardant in a HIPS/PPE blend by the UL-94 method on a ⅛ inch specimen. Melamine cyanurate (MC) was employed as a co-additive in one run. The following results were obtained:

| HIPS/PPO/FR/MC Ratio (Wt. Basis) | % P | UL-94 |
|---|---|---|
| 80/20/0/0 | 0 | Fail |
| 80/20/20/8 | 1.04 | V-1 |

The foregoing Examples, since they are intended to merely illustrate certain embodiments of the present invention, should not be construed in a limiting sense. The scope of protection sought is set forth in the Claims which follow.

We claim:
1. Di(hydroxy-o-alkylaryl) aryl phosphate.
2. Di(hydroxy-o-t-butylphenyl) phenyl phosphate.
3. Di(p-hydroxy-o-alkylaryl) aryl phosphate.
4. Di(p-hydroxy-o-t-butylphenyl) phenyl phosphate.

* * * * *